United States Patent
Alario et al.

(10) Patent No.: US 6,198,014 B1
(45) Date of Patent: *Mar. 6, 2001

(54) PROCESS FOR ISOMERIZING AROMATIC COMPOUNDS CONTAINING EIGHT CARBON ATOMS COMPRISING A RECYCLE

(75) Inventors: Fabio Alario, Neuilly sur Seine; Jean-François Joly, Lyons; Julia Magne-Drisch, Vilette de Vienne; Gérard Miquel, Saint Genis Laval; Marc Reymond, Meyzieux; Vincent Coupard, Lyons, all of (FR)

(73) Assignee: Institut Francais du Petrole, Rueil Malmaison (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/172,303

(22) Filed: Oct. 14, 1998

(30) Foreign Application Priority Data

Oct. 14, 1997 (FR) .................................................. 97 13009
Nov. 24, 1997 (FR) .................................................. 97 14820

(51) Int. Cl.⁷ .................................................. C07C 5/22
(52) U.S. Cl. .................. 585/480; 585/477; 585/478; 585/481; 585/482; 585/479
(58) Field of Search .................. 585/480, 481, 585/482, 478, 477, 479

(56) References Cited

U.S. PATENT DOCUMENTS

| | | | |
|---|---|---|---|
| 3,553,276 | 1/1971 | Berger et al. | 260/668 |
| 3,577,475 | * 5/1971 | Csicsery et al. | 260/668 |
| 4,139,571 | * 2/1979 | Riehm | 260/668 A |
| 4,255,606 | 3/1981 | Tse | 585/482 |
| 4,700,012 | 10/1987 | Onodera et al. | 585/481 |
| 4,740,650 | * 4/1988 | Pellet et al. | 585/480 |
| 5,516,957 | * 5/1996 | Dandekar et al. | 585/482 |

FOREIGN PATENT DOCUMENTS

| | | | |
|---|---|---|---|
| 0 249 914 | 12/1987 | (EP) . | |
| 851576 | * 10/1960 | (GB) | 585/480 |
| 5-016780 | * 6/1975 | (JP) | 585/480 |

* cited by examiner

*Primary Examiner*—Walter D. Griffin
*Assistant Examiner*—Thuan D. Dang
(74) *Attorney, Agent, or Firm*—Millen White Zelano & Branigan

(57) ABSTRACT

For isomerising aromatic compounds containing eight carbon atoms in the presence of hydrogen, a mixture containing compounds with a boiling point of about 80° C. to 135° C. comprising at least one paraffin containing eight carbon atoms, at least one naphthene containing eight carbon atoms, at least benzene and at least toluene is added to the feed before introducing it into the isomerisation reactor R via line 1. These additions are made by a recycle via line 6 or by adding fresh compounds via line 11, or be a combination of fresh and recycled compounds via lines 6 and 11. Hydrogen is added via line 15.

16 Claims, 1 Drawing Sheet

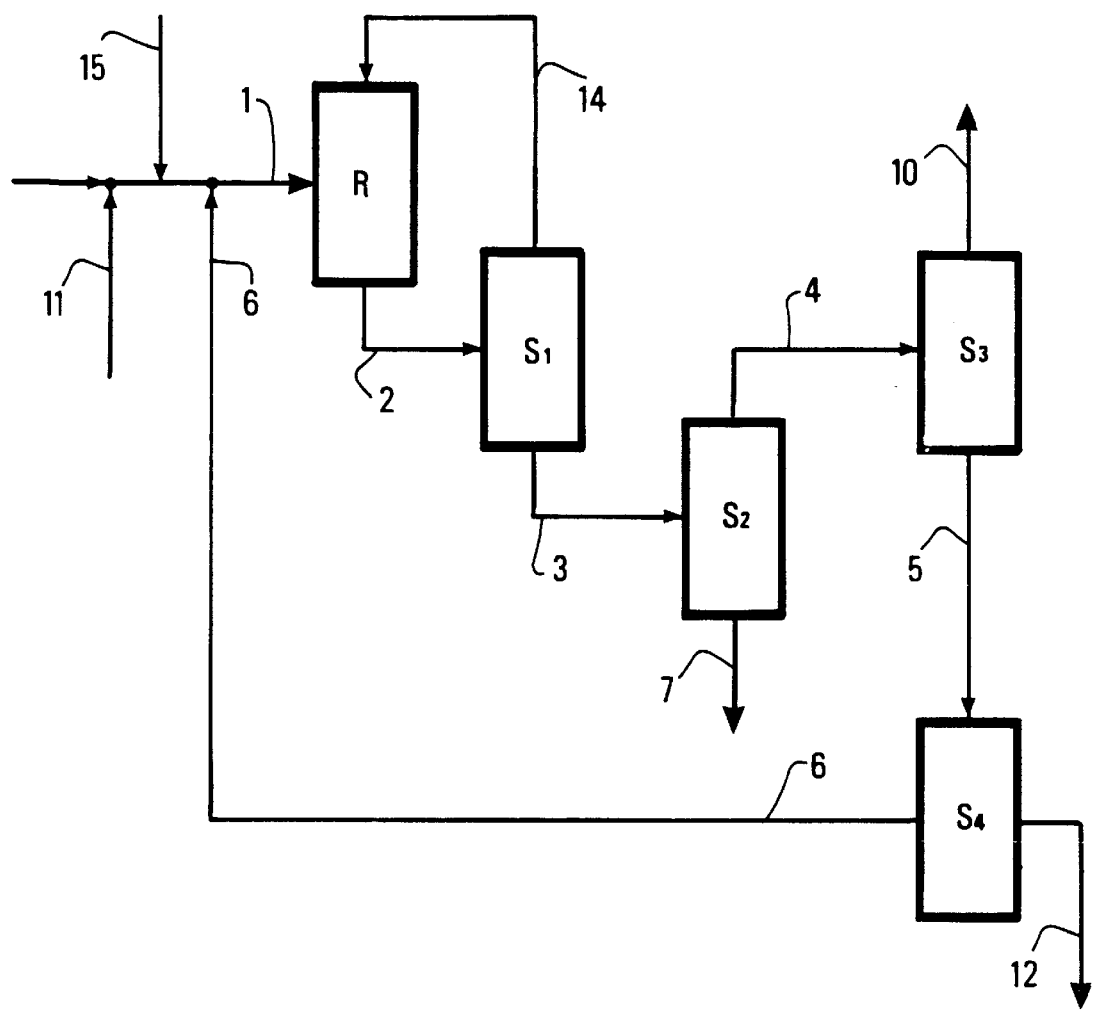

US 6,198,014 B1

PROCESS FOR ISOMERIZING AROMATIC COMPOUNDS CONTAINING EIGHT CARBON ATOMS COMPRISING A RECYCLE

FIELD OF THE INVENTION

The present invention relates to the field of isomerising aromatic compounds containing eight carbon atoms.

BACKGROUND OF THE INVENTION this field has already been the subject of much study, described in particular in U.S. patents U.S. Pat. No. 3,538,173, U.S. Pat. No. 3,553,276, U.S. Pat. No. 4,128,591 and U.S. Pat. No. 4,255,606. In known processes for isomerising aromatic compounds containing eight carbon atoms, a feed which is depleted in para-xylene with respect to the thermodynamic equilibrium of the mixture and which is rich in ethylbenzene (with respect to that same mixture at thermodynamic equilibrium) is introduced into a reactor containing at least one catalyst. That feed enters the reactor where the temperature and pressure conditions are suitable for obtaining a composition of aromatic compounds containing eight carbon atoms at the outlet from that reactor which is as close as possible to the composition of that mixture at thermodynamic equilibrium. Other documents describe processes for isomerising aromatic compounds containing eight carbon atoms in which the feed to be treated is rich in xylenes and depleted in ethylbenzene. The term "depleted in para-xylene" and "rich in ethylbenzene" as used in the present description mean that the para-xylene content is substantially lower and the ethylbenzene content is substantially higher than that of a mixture at thermodynamic equilibrium, under the temperature and pressure conditions under consideration (the mixture being constituted by meta-xylene, ortho-xylene, para-xylene and ethylbenzene).

From that mixture, the para-xylene and often the ortho-xylene are separated out since they are the isomers which are sought as they are of importance, in particular to the synthetic fibre industry. The meta-xylene and possibly the ethylbenzene can then be recycled to the isomerisation reactor inlet so as to increase the production of para-xylene and ortho-xylene.

The reaction for isomerising aromatic compounds containing eight carbon atoms per molecule, however, encounters a number of problems caused by secondary reactions. Thus in addition to the principal isomerisation reaction, hydrogenation reactions are observed: hydrogenation of aromatic compounds to naphthenes, also naphthene ring opening reactions which lead to the formation of paraffins containing at most the same number of carbon atoms per molecule as the naphthenes from which they originate. Those paraffins can undergo cracking reactions which lead to the formation of light paraffins typically containing 3 to 5 carbon atoms per molecule. Aromatic compounds undergo dismutation and transalkylation reactions which, in the case of aromatic compounds containing eight carbon atoms, lead to the production of benzene, toluene, aromatic compounds containing 9 carbon atoms per molecule (for example trimethylbenzenes) and heavier aromatic compounds.

The aggregate of such secondary reactions substantially and deleteriously affects the yields of desired products.

The quantity of secondary products formed (essentially naphthenes, paraffins, benzene, toluene, and aromatic compounds containing 9 or 10 carbon atoms per molecule) depends on the nature of the catalyst and the operating conditions of the isomerisation reactor (temperature, partial pressures of hydrogen and hydrocarbons).

An examination of the prior art documents reveals that recycling certain constituents contained in the effluent from the isomerisation reactor to the inlet of that reactor to minimise the production of secondary products has been envisaged.

As an example, U.S. Pat. No. 3,553,276, U.S. Pat. No. 3,558,173 and U.S. Pat. No. 4,255,606 recommend adding certain produces to the feed to be treated to reduce the loss due to secondary products.

U.S. Pat. No. 3,553,276 describes an apparatus in which toluene is recycled such that the concentration of toluene is kept at double the concentration which would be obtained without that recycling.

U.S. Pat. No. 3,558,173 describes recycling naphthenes containing eight carbon atoms produced by hydrogenation of the corresponding aromatic compounds to the reactor inlet.

In the description of U.S. Pat. No. 4,255,606, 1% to 10% by weight with respect to the total feed of an aliphatic hydrocarbon containing at least 5 carbon atoms per molecule is introduced into the reaction zone with or without adding toluene. This addition can be effected by recycling. The hydrocarbon introduced can also be a precursor of n-pentane.

SUMMARY OF THE INVENTION

The process of the invention for isomerising aromatic compounds containing eight carbon atoms per molecule comprises introducing into the reaction zone, with the feed containing the aromatic compounds to be isomerised and the hydrogen required for the reaction, a mixture containing compounds with a boiling point of about 80° C. to 135° C. comprising at least the following compounds:

- at least one paraffin containing eight carbon atoms per molecule;
- at least benzene;
- at least toluene;
- at least one naphthene containing eight carbon atoms.

This compound or these compounds are added to the fresh feed in the form of a recycle or in the form of fresh compounds, in quantities such that the percentages by weight of the added compounds with respect to the total feed which enters the reactor are as follows:

- the percentage of paraffins containing eight carbon atoms per molecule is about 0.1% to 10% by weight, preferably about 0.2% to 2% by weight;
- the percentage of naphthenes containing eight carbon atoms is about 0.5% to 15% by weight, preferably about 2% to 8% by weight;
- the percentage of toluene is about 0.1% to 10% by weight, preferably about 0.2% to 5% by weight;
- the percentage of benzene is about 01% to 10% by weight, preferably about 0.2% to 2% by weight.

The total percentage of added compounds represents about 0.8% to 20% by weight, normally about 2% to 15% by weight, with respect to the total feed entering the reactor.

Surprisingly, added this mixture to the feed to be treated reduces production of those very products. In particular, this addition reduces the production of paraffins containing eight carbon atoms per molecule, of aromatic compounds containing at least 9 carbon atoms per molecule, and can reduce or even stop the production of naphthenes containing eight carbon atoms per molecule.

Further, the process of the present invention enables the catalyst to be used under lower pressure and temperature conditions and at higher HSVs (weight of feed/weight of catalyst/hour), representing an advantage over prior art conditions.

The mixture containing paraffins containing eight carbon atoms per molecule, benzene, toluene and naphthenes containing eight carbon atoms per molecule can be obtained by recycling paraffins containing eight carbon atoms per molecule, benzene, toluene and naphthenes containing eight carbon atoms per molecule produced by the reaction. This mixture can also be obtained by specific addition of fresh products of by a combination of a recycle and adding fresh products.

The process of the invention has a number of advantages over the prior art, including a reduction in the loss of aromatic compounds containing eight carbon atoms per molecule by secondary side reactions of dismutation, transalkylation, hydrogenation and cracking.

In conventional processes for isomerising aromatic compounds containing eight carbon atoms, a mixture of xylenes and possibly ethylbenzene is brought into contact with a suitable catalyst generally containing a noble metal and a mineral support, to bring the mixture of aromatic compounds containing eight carbon atoms per molecule to a composition which is as close as possible to the composition corresponding to thermodynamic equilibrium at the temperature under consideration. The process of the present invention is suitable for application to all catalysts which are effective in isomerising a mixture of aromatic compounds containing eight carbon atoms per molecule, as well as catalysts which are effective in dealkylating isomerisation of ethylbenzene to benzene.

In the process of the present invention, the catalyst can be used in lower temperature ranges (370–420° C.) than in conventional processes, at lower partial pressures of hydrogen (5–12 bars absolute) than in conventional processes, and at high HSVs (weight of feed/weight of catalyst/hour) (3 to 6 $h^{-1}$) than in conventional processes.

The cuts treated in the process of the invention are injected with hydrogen into a reactor containing at least one catalyst. Examples of catalysts which can be used in the process of the invention are catalysts comprising at least one metal from group VIII of the periodic table ("Handbook of Chemistry and Physics", 45th edition, 1964–1965) such as platinum, and at least one mineral support. A zeolite is usually used as a catalyst support. Examples of suitable zeolites are mordenite, omega zeolite, and zeolite with structure type MFI. Non zeolitic molecular sieves such as crystalline aluminophosphates can also be used. These examples do not limit the choice of catalyst.

The reaction temperature is about 300° C. to 500° C., preferably about 35° C. to 450° C., more preferably about 370° C. to 420° C., the partial pressure of hydrogen is about 3 to 15 bars absolute, preferably about 4 to 12 bars and more preferably 7 to 12 bars absolute, the total pressure is about 4 to 20 bars absolute, preferably 6 to 15 bars absolute, the HSV (weight of fee/weight of catalyst/hour) is about 0.2 to 10 $h^{-1}$, preferably about 1 to 15 $h^{-1}$, and more preferably 3 to 6 $h^{-1}$.

In a variation of the process of the present invention, the process of the present invention can comprise a dehydrogenation step carried out after the isomerization step.

Thus in this particular implementation of the process of the present invention, the present invention provides a process for isomerising a feed comprising aromatic compounds containing eight carbon atoms, comprising at least one isomerisation step a) and at least one hydrogenation step b).

Any catalyst which can dehydrogenate naphthene type compounds to aromatic compounds can be used in step b) of the process of the present invention. At the dehydrogenation reactor outlet, for a given number of carbon atoms per molecule, the aromatic compounds obtained are present in the proportions of thermodynamic equilibrium under the temperature and pressure conditions reigning at the outlet from the reactor.

Thus in a first step of the process, the operating conditions in the isomerisation zone are selected so as to minimise the production of unwanted compounds from reactions which involve acid catalysis reactions (cracking, dealkylation, dismutation, . . . ). These operating conditions are such that production of naphthenes containing eight carbon atoms per molecule is significantly higher—about 10% to 30% by weight of the effluent at the outlet form the isomerisation zone—than the production obtained by conventional processes for isomerising aromatic compounds containing eight carbon atoms—which is generally about 5% to 10% by weight of the effluent at the outlet from the isomerisation zone.

The effluent obtained from the first reaction zone is treated in a second step in a reaction zone containing at least one dehydrogenation catalyst. The operating conditions for this second step may be identical to or different from the operating conditions in the first step; preferably the operating conditions in these two steps are different. The operating conditions in this second step are determined so as to obtain a xylene and ethylbenzene mixture composition which is as close as possible to the composition at thermodynamic equilibrium.

Catalysts for dehydrogenating paraffins and naphthenes are well known to the skilled person. The supports for these catalysts are generally refractory oxides, usually an alumina. These dehydrogenation catalysts comprise at least one noble metal from group VIII of the periodic table and at least one alkali or alkaline-earth element from groups Ia and IIa of the periodic table. The noble group VIII metal is preferably platinum, and the element from groups Ia or IIa of the periodic table is selected from the group formed by magnesium, potassium and calcium.

These dehydrogenation catalysts can also contain thorium and/or at least one element M from groups IVa or IVb of the periodic table. The group IVa or IVb elements are usually selected from the group formed by tin, silicon, titanium and zirconium. Certain dehydrogenation catalysts also contain sulphur and/or a halogen. More particularly, dehydrogenation catalysts described in U.S. patents U.S. Pat. No. 3,998,900 and U.S. Pat. No. 3,531,543 can be used in the dehydrogenation step of the process of the invention.

Without wishing to be tied to a particular theory, it can be noted that platinum has a hydrogenolysing activity which is expressed to the detriment of the activity for dehydrogenation of paraffins to aromatic compounds. This hydrogenolysing activity can be substantially reduced, and the selectivity of the catalyst as regards the dehydrogenation reaction can be increased, by adding additional element M.

The inorganic refractory supports used often have an acidic nature and can generate unwanted secondary reactions such as cracking or isomerisation reactions. For this reason, the oxide support is generally neutralised by adding at least one alkaline or alkaline-earth element.

The dehydrogenation step is carried out in the presence of hydrogen which can be introduced in the form of fresh hydrogen, in the form of hydrogen recycled from the outlet from the isomerization zone or in the form of hydrogen recycled from the outlet from the isomerisation zone or in the form of hydrogen recycled from the outlet from the dehydrogenation zone.

The operating conditions for the dehydrogenation step are: a temperature of about 300° C. to 500° C., preferably about 400° C. to 420° C., an absolute partial pressure of hydrogen of about 1 to 15 bars, preferably about 4 to 10 bars, a total absolute pressure of about 2 to 20 bars, preferably about 5 to 15 bars, and an HSV (weight of feed/weight of catalyst/hour) of about 0.2 to 10 $h^{-1}$, preferably about 3 to 6 $h^{-1}$.

Further, aromatic compounds containing eight carbon atoms contained in the effluent from the dehydrogenation zone can also be recycled after having extracted the desired compounds, i.e., para-xylene and possibly ortho-xylene.

BRIEF DESCRIPTION OF THE DRAWING

The FIGURE shows a block flowsheet of a simple embodiment of the process of the invention.

DETAILED DESCRIPTION OF FIGURE

In the FIGURE, fresh feed containing the mixture of aromatic compounds containing eight carbon atoms to be isomerised is introduced into the reactor R via line 1. Before being injected into the isomerisation reactor R, this fresh feed is enriched with a mixture containing the following compounds: at least one paraffin containing eight carbon atoms per molecule, benzene, toluene and at least one naphthene containing eight carbon atoms per molecule. These additions are carried out by means of a recycle via line 6 or by adding fresh compounds via line 11 or by a combination of fresh and recycled compounds by means of these two lines 6 and 11. Hydrogen is added via line 15.

After reaction, the effluent is sent to a separation zone $S_1$. In zone $S_1$, hydrogen contained in the effluent is isolated and recycled to the inlet to the reactor via line 14, the remaining effluent being sent to a separation zone $S_2$ via line 3. In separation zone $S_2$, the reaction products are separated into two fractions: a light fraction which contains paraffins, naphthenes and the lightest aromatic compounds such as benzene and toluene which are sent to a separation zone $S_3$ via line 4; the other fraction comprises aromatic compounds containing at least eight carbon atoms. Following successive separation steps, the desired products, in particular para-xylene, will be separated from this fraction.

In one separation zone $S_3$, hydrocarbons containing one to seven carbon atoms per molecule are separated (and evacuated via line 10) from the phase comprising paraffins containing eight carbon atoms per molecule, naphthenes containing eight carbon atoms per molecule, benzene and toluene. This mixture is sent via line 5 to a separation zone $S_4$. In separation zone $S_4$, the quantities of paraffins containing eight carbon atoms per molecule, benzene, toluene and naphthenes containing eight carbon atoms per molecule which are to be recycled are selected. This mixture is then sent via line 6 upstream of the reactor where it enriches the fresh feed (a portion of the fraction from $S_2$ comprising aromatic compounds containing eight carbon atoms per molecule and from which the desired products, in particular para-xylene, have been extracted, has already been added to the fresh feed). A line 12 is provided to evacuate the portion of the mixture comprising paraffins containing eight carbon atoms per molecule, naphthenes containing eight carbon atoms per molecule, benzene and toluene which is not to be recycled.

The following examples illustrate the invention without limiting its scope.

EXAMPLES

The catalyst used in the following examples was an alumina based catalyst containing mordenite and 0.4% by weight of platinum, the catalyst being present in the form of extrudates.

Examples 1 and 2

Examples 1 and 2 were carried out under the following operating conditions: a temperature of 385° C., a total pressure of 8 bars absolute and a molar ratio of hydrogen to hydrocarbons of 4/1.

In Example 1, a feed 1 was used the composition of which is shown in the following table. In Example 2, a feed 2 was treated which was substantially identical to that of feed 1 however, 1% of paraffins containing eight carbon atoms per molecule with respect to the total feed entering the reactor was added.

|  | EXAMPLE 1 | | EXAMPLE 2 | |
| --- | --- | --- | --- | --- |
| Compounds | Feed 1 (wt %) | Products (wt %) | Feed 2 (wt %) | Products (wt %) |
| C1–C4 paraffins | — | 0.45 | — | 0.7 |
| i-pentane | — | 0.1 | — | 0.2 |
| n-pentane | — | 0.1 | — | 0.1 |
| Benzene | — | 0.3 | — | 0.3 |
| Toluene | 0.2 | 1.1 | 0.25 | 0.9 |
| o-xylene | 25.3 | 18.8 | 25.1 | 19.4 |
| m-xylene | 56.5 | 42.0 | 56.3 | 42.4 |
| p-xylene | 1.5 | 17.7 | 1.5 | 16.8 |
| Ethylbenzene | 14.0 | 9.0 | 13.6 | 9.7 |
| C6 naphthenes | — | 0.2 | — | 0.1 |
| C7 naphthenes | — | 0.2 | — | 0.1 |
| C8 paraffins | 0.1 | 0.37 | 1.1 | 1.2 |
| C8 naphthenes | 2.0 | 7.6 | 1.9 | 6.7 |
| C9 + aromatic compounds | 0.1 | 1.9 | — | 0.6 |

In Example 1, losses in the form of paraffins containing eight carbon atoms per molecule were 0.28% by weight with respect to the quantity of aromatic compounds containing eight carbon atoms per molecule introduced into the reactor; in Example 2, these losses were 0.10% by weight.

By adding 1% by weight of paraffins containing eight carbon atoms per molecule with respect to the total feed entering the reactor (Example 2), losses in the form of paraffins containing eight carbon atoms per molecule were reduced by 0.18% by weight with respect to the isomerisation carried out without additions (Example 1).

Examples 3 and 4

Examples 3 and 4 were carried out under the following operating conditions: a temperature of 390° C., a total pressure of 9 bars absolute and a molar ratio of hydrogen to hydrocarbons of 4/1. In Example 3, a feed 3 was used the composition of which is shown in the following table. In Example 4, a feed 4 was treated which was substantially identical to that of feed 3, however 1.8% by weight of naphthenes containing eight carbon atoms per molecule with respect to the total feed entering the reactor was added, also 1.2% by weight of toluene with respect to the total feed entering the reactor was added.

| Compounds | EXAMPLE 3 | | EXAMPLE 4 | |
|---|---|---|---|---|
| | Feed 3 (wt %) | Products (wt %) | Feed 4 (wt %) | Products (wt %) |
| C1–C4 paraffins | — | 0.6 | — | 0.3 |
| i-pentane | — | 0.1 | — | 0.2 |
| n-pentane | — | 0.1 | — | 0.1 |
| Benzene | — | 0.3 | — | 0.3 |
| Toluene | 0.2 | 1.1 | 1.4 | 1.8 |
| o-xylene | 25.3 | 19.1 | 24.5 | 19.3 |
| m-xylene | 56.5 | 42.0 | 54.9 | 41.7 |
| p-xylene | 1.5 | 17.7 | 1.5 | 16.6 |
| Ethylbenzene | 14.0 | 9.5 | 13.6 | 9.9 |
| C6 naphthenes | — | 0.1 | — | 0.1 |
| C7 naphthenes | — | 0.2 | — | 0.3 |
| C8 paraffins | 0.1 | 0.3 | 0.1 | 0.3 |
| C8 naphthenes | 2.0 | 6.9 | 3.8 | 6.75 |
| C9 + aromatic compounds | 0.1 | 1.9 | 0.1 | 1.5 |

In Example 3, losses in the form of naphthenes containing eight carbon atoms per molecule were 5.03% by weight with respect to the quantity of aromatic compounds containing eight carbon atoms per molecule introduced into the reactor and losses in the form of toluene were 0.92% by weight with respect to the quantity of aromatic compounds containing eight carbon atoms per molecule introduced into the reactor; in Example 4, losses in the form of naphthenes containing eight carbon atoms per molecule were 3.12% by weight with respect to the total quantity of aromatic compounds containing eight carbon atoms per molecule introduced into the reactor and losses in the form of toluene were 0.42% by weight with respect to the quantity of aromatic compounds containing eight carbon atoms per molecule introduced into the reactor.

By adding 1.8% by weight of naphthenes containing eight carbon atoms with respect to the total feed entering the reactor and 1.2% by weight of toluene with respect to the total feed (Example 4), losses in the form of naphthenes containing eight carbon atoms per molecule were reduced by 1.91% by weight and losses in the form of toluene by 0.5% by weight with respect to isomerisation carried out without additions (Example 3).

Example 5

Example 5 illustrates the influence of recycling a cut with a distillation range of about 80° C. to 135° C. on losses of aromatic compounds containing eight carbon atoms per molecule. These examples were executed under the following operating conditions: a temperature of 385° C., and a total pressure of 8 bars absolute with a molar ration of hydrogen to hydrocarbons of 4/1. In Example 5, a recycle, corresponding to 9% by weight of the cut leaving reactor R and which contained a mixture comprising paraffins containing eight carbon atoms per molecule, benzene, toluene and naphthenes containing eight carbon atoms per molecule obtained after separation from the effluent from reactor R, was added via line 6 to the feed entering the reactor. The composition of feed 5 of Example 5 is shown in the table below.

| Compounds | EXAMPLE 5 | |
|---|---|---|
| | Feed 5 (wt %) | Products (wt %) |
| C1–C4 paraffins | — | 0.7 |
| i-pentane | — | 0.2 |
| n-pentane | — | 0.1 |
| Benzene | 0.1 | 0.3 |
| Toluene | 2.0 | 2.4 |
| o-xylene | 22.8 | 18.7 |
| m-xylene | 52.0 | 41.3 |
| p-xylene | 1.6 | 16.8 |
| Ethylbenzene | 13.2 | 9.4 |
| C6 naphthenes | — | 0.2 |
| C7 naphthenes | 0.1 | 0.5 |
| C8 paraffins | 0.4 | 0.5 |
| C8 naphthenes | 7.5 | 7.3 |
| C9 + aromatic compounds | 0.1 | 1.6 |

In Example 1, losses in the form of naphthenes containing eight carbon atoms were 5.75% by weight with respect to the quantity of aromatic compounds containing eight carbon atoms per molecule introduced into the reactor, losses in the form of aromatic compounds and naphthenes with a carbon chain containing a number of carbon atoms per molecule other than eight (essentially losses in the form of benzene, toluene, naphthenes containing six or seven carbon atoms and aromatic compounds containing at least nine carbon atoms) were 3.49% by weight with respect to the quantity of aromatic compounds containing eight carbon atoms per molecule introduced into the reactor, and the yield of aromatic compounds containing eight carbon atoms was 90% by weight. In Example 5, losses in the form of naphthenes containing eight carbon atoms per molecule were 0.22% by weight with respect to the quantity of aromatic compounds containing eight carbon atoms per molecule introduced into the reactor, and losses in the form of aromatic compounds and naphthenes with a carbon chain containing a number of carbon atoms per molecule other than eight were 3.01% by weight with respect to the quantity of aromatic compounds containing eight carbon atoms per molecule introduced into the reactor.

The yield of aromatic compounds containing eight carbon atoms per molecule was 96.2% by weight.

Thus by adding a recycle, corresponding to 9% by weight of the cut leaving reactor R and which contained a mixture comprising paraffins containing eight carbon atoms per molecule, benzene, toluene and naphthenes containing eight carbon atoms per molecule obtained after separation from the effluent from reactor R, the feed entering the reactor (Example 5), losses of naphthenes containing eight carbon atoms per molecule were reduced by 5.53% by weight and losses in the form of aromatic compounds and naphthenes in which the carbon chain contained a number of carbon atoms per molecule other than eight were reduced by 0.48% by weight with respect to isomerisation carried out without addition (Example 1). The yield by weight of aromatic compounds containing eight carbon atoms per molecule was increased by 6.2%.

Example 6

Example 6 illustrates the influence of recycling a cut with a distillation range of about 80° C. to 135° C. combined with adding toluene on losses of aromatic compounds containing eight carbon atoms per molecule. These examples were executed under the following operating conditions: a temperature of 385° C., and a total pressure of 8 bars absolute with a molar ratio of hydrogen to hydrocarbons of 4/1. In Example 6, a recycle, corresponding to 9% by weight of the cut leaving reactor R and which contained a mixture comprising paraffins containing eight carbon atoms per molecule, benzene, toluene and naphthenes containing eight carbon atoms per molecule obtained after separation from the effluent from reactor R, was added via line 6 to the feed entering the reactor. In addition, 1% by weight of fresh toluene was added to the feed entering the reactor. The composition of feed 6 of Example 6 is shown in the table below.

|  | EXAMPLE 6 | |
|---|---|---|
| Compounds | Feed 6 (wt %) | Products (wt %) |
| C1–C4 paraffins | — | 0.6 |
| i-pentane | — | 0.2 |
| n-pentane | — | 0.1 |
| Benzene | 0.1 | 0.3 |
| Toluene | 2.9 | 3.1 |
| o-xylene | 22.7 | 18.6 |
| m-xylene | 51.6 | 40.9 |
| p-xylene | 1.6 | 16.8 |
| Ethylbenzene | 13.0 | 9.2 |
| C6 naphthenes | — | 0.2 |
| C7 naphthenes | 0.1 | 0.6 |
| C8 paraffins | 0.4 | 0.5 |
| C8 naphthenes | 7.4 | 7.2 |
| C9 + aromatic compounds | — | 1.6 |

In Example 6, losses in the form of naphthenes containing eight carbon atoms were 0.22% by weight with respect to the quantity of aromatic compounds containing eight carbon atoms per molecule introduced into the reactor, losses in the form of aromatic compounds and naphthenes with a carbon chain containing a number of carbon atoms per molecule other than eight were 3.03% by weight with respect to the quantity of aromatic compounds containing eight carbon atoms per molecule introduced into the reactor, and the yield of aromatic compounds containing eight carbon atoms was 96.2% by weight. Thus by adding a recycle, corresponding to 9% by weight of the cut leaving reactor R and which contained a mixture comprising paraffins containing eight carbon atoms per molecule, benzene, toluene and naphthenes containing eight carbon atoms per molecule obtained after separation from the effluent from reactor R, also 1% by weight of fresh toluene, to the feed entering the reactor, losses of naphthenes containing eight carbon atoms per molecule were reduced by 5.52% by weight and losses in the form of aromatic compounds and naphthenes in which the carbon chain contained a number of carbon atoms per molecule other than eight were reduced by 0.56% by weight with respect to isomerisation carried out without addition (Example 1). The yield of aromatic compounds containing eight carbon atoms per molecule was increased by 6.2%.

The results from the Examples are summarized in the following table:

| Losses (% by wt.) | Ex. 1 | Ex. 2 | Ex. 3 | Ex. 4 | Ex. 5 | Ex. 6 |
|---|---|---|---|---|---|---|
| of paraffins containing 8 carbon atoms | 0.28 | 0.1 | 0.2 | 0.21 | 0.11 | 0.11 |
| of naphthenes containing 8 carbon atoms | 5.75 | 5 | 5.03 | 3.12 | 0.22 | 0.22 |
| of toluene | 0.92 | 0.67 | 0.92 | 0.42 | 0.45 | 0.22 |
| yield of aromatics containing 8 carbon atoms (% by wt) | 90 | 91.5 | 90.4 | 92.6 | 96.2 | 9.62 |

Examples 1 and 3 were executed without additions to the feed, Examples 2 and 4 were executed with specific additions as already carried out in the prior art; Examples 5 and 6 were carried out with additions of compounds, in particular with a recycle of a fraction of the effluent from the reactor; Examples 5 and 6 are in accordance with the invention. It can be seen that the process of the invention can reduce losses, in particular of paraffins containing eight carbon atoms per molecule, of naphthenes containing eight carbon atoms per molecule, and of toluene, the process also increasing the yield of aromatic compounds containing eight carbon atoms per molecule.

What is claimed is:

1. A process for catalytically isomerizing aromatic compounds containing eight carbon atoms per molecule, in an isomerization reactor, comprising adding hydrogen and a recycle mixture to an aromatic feed to be isomerized at the reactor inlet, said recycle mixture consisting essentially of compounds having a boiling point range of about 80° C. to 135° C. comprising at least one acyclic paraffin containing eight carbon atoms per molecule, at least one naphthene containing eight carbon atoms per molecule, at least benzene and at least toluene, and being devoid of (a) aromatic hydrocarbons containing at least eight carbon atoms per molecule and (b) paraffinic hydrocarbons containing 1–7 carbon atoms per molecule, the catalyst used being a catalyst comprising at least one metal from group VIII of the periodic table and at least one support so as to obtain an isomerizate containing compounds having a boiling point range of about 80° to 135° C. and compounds having a boiling point outside of said boiling point range of about 80° C. to 135° C., said recycle mixture being obtained, at least partially, by recycling a fraction separated from the resulting effluent leaving the isomerization reaction.

2. A process for isomerising aromatic compounds containing eight carbon atoms per molecule according to claim 1, characterized in that the recycle mixture added to the aromatic feed containing at least one acyclic paraffin containing eight carbon atoms per molecule, at least benzene, at least toluene and at least one naphthene containing eight carbon atoms per molecule is obtained exclusively by recycling a fraction containing said compounds isolated from the effluent leaving the isomerisation reactor.

3. A process for isomerising aromatic compounds containing eight carbon atoms per molecule according to claim 1, wherein characterized in that the recycle mixture added to the aromatic feed containing at least one acyclic paraffin containing eight carbon atoms per molecule, at least benzene, at least toluene and at least one naphthene containing eight carbon atoms per molecule is obtained by recycling the fraction containing said compounds isolated from the effluent leaving the isomerisation reactor and by adding fresh products.

4. A process for isomerising aromatic compounds containing eight carbon atoms per molecule according to claim 1, wherein the recycle mixture added to the aromatic feed is such that the total percentage by weight of the added compounds is about 0.8% to 20%.

5. A process for isomerising aromatic compounds containing eight carbon atoms per molecule according to claim 1, wherein the recycle mixture added to the aromatic feed is such that the percentage by weight of acyclic paraffins containing eight carbon atoms per molecule added with respect to the total feed entering the reactor is about 0.1% to 10%, the percentage by weight of naphthenes containing eight carbon atoms per molecule added with respect to the total feed entering the reactor is about 0.5% to 15%, the percentage by weight of toluene added with respect to the total feed entering the reactor is about 0.1% to 10%, and the percentage by weight of benzene with respect to the total feed entering the reactor is about 0.1% to 10%.

6. A process for isomerising aromatic compounds containing eight carbon atoms per molecule according to claim 1, wherein the reaction temperature is about 300° C. to 500° C., the partial pressure of hydrogen is about 3 to 15 bars absolute, the total pressure is about 4 to 20 bars absolute, and the HSV (weight of feed/weight of catalyst/hour) is about 0.2 to 10 $h^{-1}$.

7. A process for isomerising aromatic compounds containing eight carbon atoms per molecule according to claim 1, wherein the catalyst support comprises a zeolite.

8. A process for isomerising aromatic compounds containing eight carbon atoms per molecule according to claim 1, wherein the catalyst is a non zeolitic molecular sieve.

9. A process for isomerising aromatic compounds containing eight carbon atoms per molecule according to claim 5, wherein the reaction temperature is about 300° C. to 500° C., the partial pressure of hydrogen is about 3 to 15 bars absolute, the total pressure is about 4 to 20 bars absolute, and the HSV (weight of feed/weight of catalyst/hour) is about 0.2 to 10 $h^{-1}$.

10. A process for isomerising aromatic compounds containing eight carbon atoms per molecule according to claim 9, wherein the catalyst support comprises a zeolite.

11. A process for isomerising aromatic compounds containing eight carbon atoms per molecule according to claim 9, wherein the catalyst support is a non zeolitic molecular sieve.

12. A process according to claim 1, further comprising the following steps in order to provide said fraction separated from the resulting effluent leaving the isomerization reactor:
(a) recovering an isomerization product from the isomerization reactor;
(b) subjecting said effluent to separation steps so as to recover the following fractions, a hydrogen fraction, a fraction containing mainly aromatic compounds containing at least 8 carbon atoms, a fraction containing mainly $C_{1-7}$ paraffins, and a fraction consisting of a cut having a boiling point range of about 80° C. to 135° C. comprising at least one acyclic paraffin containing eight carbon atoms per molecule, at least one naphthene containing eight carbon atoms per molecule, at least benzene and at least toluene, and being devoid of aromatic hydrocarbons containing at least eight carbon atoms per molecule, and recycling a partial stream of the latter fraction to the isomerization reactor.

13. A processing according to claim 1, further comprising the following steps for separating a recycle fraction from the resulting effluent leaving the isomerization reactor:
(a) recovering an effluent from the isomerization reactor;
(b) separating a hydrogen stream from said effluent;
(c) subjecting the resultant hydrogen-depleted isomerization effluent to distillation so as to recover a bottoms product containing mainly aromatic hydrocarbons having at least eight carbon atoms and an overhead stream containing a mixture comprising $C_{1-8}$ paraffins, benzene, toluene and naphthenes containing eight carbon atoms per molecule;
(d) passing said overhead stream to a separator to remove $C_{1-7}$ paraffins; and
(e) separating a $C_{1-7}$ paraffin depleted cut having a distillation range of about 80° C. to 135° C., and a recycling a partial stream of said cut to the isomerization reactor.

14. A process according to claim 1, wherein said mixture comprises (a) said fraction separated from the resulting effluent leaving the isomerization reactor and (b) fresh toluene.

15. A processing according to claim 2, further comprising the following steps for separating a recycle fraction from the resulting effluent leaving the isomerization reactor:
(a) recovering an effluent from the isomerization reactor;
(b) separating a hydrogen stream from said effluent;
(c) subjecting the resultant hydrogen-depleted isomerization effluent to distillation so as to recover a bottoms product containing mainly aromatic hydrocarbons having at least eight carbon atoms and an overhead stream containing a mixture comprising $C_{1-8}$ paraffins, benzene, toluene and naphthenes containing eight carbon atoms per molecule;
(d) passing said overhead stream to a separator to remove $C_{1-7}$ paraffins; and
(e) separating a $C_{1-7}$ paraffin depleted cut having a distillation range of about 80° C. to 135° C., and a recycling a partial stream of said cut to the isomerization reactor.

16. A processing according to claim 14, further comprising the following steps for separating a recycle fraction from the resulting effluent leaving the isomerization reactor:
(a) recovering an effluent from the isomerization reactor;
(b) separating a hydrogen stream from said effluent;
(c) subjecting the resultant hydrogen-depleted isomerization effluent to distillation so as to recover a bottoms product containing mainly aromatic hydrocarbons having at least eight carbon atoms and an overhead stream containing a mixture comprising $C_{1-8}$ paraffins, benzene, toluene and naphthenes containing eight carbon atoms per molecule;
(d) passing said overhead stream to a separator to remove $C_{1-7}$ paraffins; and
(e) separating a $C_{1-7}$ paraffin depleted cut having a distillation range of about 80° C. to 135° C., and a recycling a partial stream of said cut to the isomerization reactor.

* * * * *